United States Patent [19]

Del Soldato et al.

[11] Patent Number: 5,019,579

[45] Date of Patent: May 28, 1991

[54] PHARMACEUTICAL COMPOSITIONS CONTAINING DEXTRORPHAN FOR INTRANASAL APPLICATION

[75] Inventors: Piero Del Soldato, Monza; Silvano Casadio, Milan, both of Italy

[73] Assignee: Prodotti Formeti S.R.L., Milan, Italy

[21] Appl. No.: 445,106

[22] Filed: Dec. 7, 1989

Related U.S. Application Data

[63] Continuation of Ser. No. 910,986, Sep. 24, 1986, abandoned.

[30] Foreign Application Priority Data

Sep. 26, 1985 [IT] Italy ........................ 22288 A/85

[51] Int. Cl.⁵ .............................. A61K 31/44
[52] U.S. Cl. ............................. 514/289; 514/947
[58] Field of Search ...................... 514/289, 947

[56] References Cited

U.S. PATENT DOCUMENTS 4,454,140 6/1984 Goldberg et al. ............... 514/289

OTHER PUBLICATIONS

Shanker et al.,–Journal of Pharmacology and Experimental Therapeutics: 120, 528, 1957.
Goodman and Gilman–"The Pharmacological Basis of Therapeutics", 6th ed., 1980, pp. 513, 529.

*Primary Examiner*—Leonard Schenkman
*Attorney, Agent, or Firm*—Cushman, Darby & Cushman

[57] ABSTRACT

The object of the invention is a pharmaceutically acceptable composition suitable to achieve a systemic therapeutical response due to its antitussis action in warm-blooded animals, characterized in that it contains, per dosage unit: (I) an amount therapeutically efficacious by systemic way due to the antitussis action of salified dextrorphan, and (II) a pharmaceutically non-toxic excipient acceptable for intranasal administering.

10 Claims, No Drawings

PHARMACEUTICAL COMPOSITIONS CONTAINING DEXTRORPHAN FOR INTRANASAL APPLICATION

This is a continuation of application Ser. No. 06/910,986, filed Sept. 24, 1986 now abandoned.

BACKGROUND OF THE INVENTION

Dextrorphan is the dextro isomer of levorphan, this latter being an opium substance endowed with marked analgesic activity. Differently from levorphan, dextrorphan does not have any analgesic activity, nor has it any affinity for the opium receptors (and therefore it causes neither dependence nor tolerance) (Benson W. M., Stefko P. L., Randall L. O.; J. Pharmacol. Exp. Therap. 109, 189, 1953), but is endowed with a considerable antitussis action (Goodman L. S., Gilman A.: "The Pharmacological Basis of Therapeutics", page 263, Mc-Millan Pub. Co. Inc., New York 1975).

Many investigations have shown that this compound, either in free or in conjugated form, is the major metabolite of dextromethorphan (Axelrod J., J. Pharmacol. Exp. Ther. 117, 322, 1956; Elison C., Elliott, J., Pharmacol. Exp. Ther. 144, 265, 1964; Kamm J., Taddeo A., Van Loon E., J. Pharmacol. Exp. Ther. 158, 437, 1967; Willner, Arzneim. Forsch. 13, 20, 1963), a drug which has been marketed worldwide as a sedative for tussis. It has been demonstrated indeed (Aylward M., Maddock J., Davies D. E., Protheroe D. A., Leideman T.; Eur. J. Respir. Dis. 65, 283, 1984) that the clinical efficaciousness of dextromethorphan is best correlated not to its hematic levels (which are practically negligible in correspondence of the peak time of the therapeutical effects), but to the hematic levels of dextrorphan, so that the concentration of said metabolite in the biological fluids is commonly determined for the kinetic study of dextromethorphan (Ramachander G., Williams F. D., Emele J. F.; J. Pharm. Sci. 66, 1047, 1977). The hematic levels of dextrorphan which are observed after the oral administering of dextromethorphan remain stable over longer, than three hours. But it must be remembered that the metabolic conversion of dextromethorphan into dextrorphan does not occur always in a constant and foreseeable way. In fact, this reaction depends on sex (Ramachander G., Bapatla K. R., Emele J. F.; J. Pharm. Sci. 67, 1326, 1978), i.e., it is much faster in male sex, and, like all the metabolic reactions of the exogenous substances, it can be influenced by the state of health of the patient, by his age, etc. (Goodman L. S., Gilman A.: "The Pharmacological Basis of Therapeutics", pages 16-17, Mc Millan Int. Co., New York 1975).

Another interesting consideration is that dextrorphan has a toxicity by parenteral way even lower than dextromethorphan (Benson W. M., Stefko P. L., Randall L. O.; J. Pharmacol. Exp. Therap., 109, 189, 1953). One could thus think to directly use dextrorphan as a tussis sedative agent.

But a severe hindrance to a therapeutical use thereof is constituted by the fact that this component is not absorbed when it is administered by oral way (Schanker L. S., Shore Parkhurst P. A., Brodie B. B., Hoghen C. A. M., J. Pharmacol. Exp. Therap., 120, 528, 1957).

SUMMARY OF THE INVENTION

To obviate this drawback, the present invention proposes to use for dextrorphan the intranasal administering way, which allows the product to come, integer and in substantial amount, to the effector organ. According to the invention it has been observed indeed that the intranasal administration of pharmaceutical compositions containing dextrorphan has as its effect a high bioavailability of the active principle. These results lead to an excellent therapeutical performance, comparable to that deriving from the parenteral administering.

Surprisingly, it has been found according to the invention that dextrorphan can be efficaciously administered by intranasal way, in suitable pharmaceutical compositions.

DETAILED DESCRIPTION OF PREFERRED EMBODIMENTS

More specifically, the inventors found that salified dextrorphan can be advantageously formulated in new dosage forms for intranasal administration, to the purpose of producing an improved bioavailability and homogeneity of its hematic levels, relatively to the oral formulation. The new forms of administering of the present invention can be solutions, suspensions, ointments, gels, nebulized aerosols, fitted to the intranasal application. Thus, for an aspect thereof, the present invention supplies a pharmaceutically acceptable nasal-release composition, in a form of unitary dosage, for the intranasal administering, to the purpose of obtaining an antitussis effect in warm-blooded animals:

I) by the use of a therapeutically efficacious amount of active principle, substantially dextrorphan salts, as better specified in the descriptive section of the invention;

II) non-toxic and pharmaceutically acceptable nasal carriers.

For another aspect thereof, the present invention relates to compositions for intranasal application of pharmaceutical quality, in form of unitary dosage, for intranasal administering, having as their purpose the obtaining of a systemic therapeutical response:

I) in warm-blooded animals by the use of salified dextrorphan—which shall be better specified in the detailed description of the invention—used as antitussis agent;

II) by the use of non-toxic and pharmaceutically valid nasal carriers, viz., pharmaceutical compositions comprising nasal ointments, nasal gels and pressurized aerosols.

For still another aspect thereof, the present invention supplies a system to obtain a systemic therapeutical response in warm-blooded animals in the therapy which uses antitussis drugs, by resorting to the use of dextrorphan salts, better specified in the detailed disclosure of the invention, administered by intranasal way, in combination with non-toxic and pharmaceutically valid nasal carriers.

The compound selected for the use in the compositions and in the systems of the present invention is dextrorphan, which can be represented by the following structural formula:

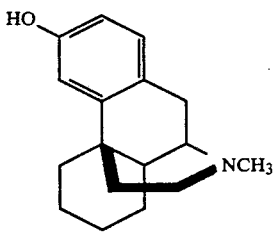

The compound can be salified by a whatever acid, e.g., tartaric acid.

According to the present invention, dextrorphan, as a salt (e.g., as the tartrate), can be administered by intranasal way with considerably higher results than those obtainable after the oral administration, in terms of increased bioavailability of the active principle, and minimization of the variations in hematic levels.

It appears well evident that the above mentioned compound is rapidly absorbed by the nasal mucosa into the systemic hematic circulation without first-pass metabolism. The above mentioned compound can be conveniently administered by intranasal way to warm-blooded animals by means of formulations suitable to be administered by intranasal application, formulations which comprise the dextrorphan salt in the proper amount to perform the antitussis effect, together with a pharmaceutically acceptable and non-toxic carrier.

The choice of the traditionally acceptable and non-toxic carriers, which does not exclude the use of carriers traditionally mentioned in the art of nasal administration, depends on the chemical-physical characteristics of the dextrorphan salt, on the required posology, on the type of selected formulation (solution, nasal gel, nasal ointment, spray aerosol, etc.), on the stability of the same salt, etc. The preferred dosage forms by intranasal way are the solutions, creams, and the gels which contain a major water amount besides the active principle. Minor amounts of other ingredients, such as preservatives, buffering agents, wetting agents and gelifiers can be sometimes present. This type of composition can be used in the management of tussis.

Compatibly with the nature and the complexity of the formulation, it is preferable that the formulation be isotonic.

The carriers on prevailingly aqueous and low-viscosity basis, as well as those using propellants on the basis of halocarbons, tend to increase the absorption rate.

The carriers based on gelified matrices, on Oil/Water (O/W) or W/O emulsions, used for direct intranasal application or by atomization, allow effects more prolonged over time to be obtained, without penalizing the fastness of these effects to any significant extent.

Of course, the therapeutical dosage range for the nasal administration of dextrorphan, according to the present invention, shall vary with the weight of the patient, and with the patient's condition the drug is administered for. The typical dosage for dextrorphan could be comprised within the range of from 10 to 100 mg, for administering by nasal way twice or three times per day.

Of course, the amount of form of nasal dosage to release the desired dosis shall depend on the concentration of the drug in the composition. For example, the volume of solution or of gel necessary to release dextrorphan in the above detailed doses shall range from 0.1 to 1.0 g of solution and/or cream or salve or gel at 10%.

Examples of the preparation of typical nasal compositions containing dextrorphan hydrochloride are reported hereunder. These Examples are supplied to illustrative purposes and they are certainly not limitative of the invention, because many modifications as regards the materials and the accomplishing processes can be realized by those skilled in the art.

EXAMPLES

Example 1

| | |
|---|---|
| Dextrorphan tartrate | 10 g |
| Methyl p.hydroxybenzoate | 0.08 g |
| Propyl p.hydroxybenzoate | 0.02 g |
| Glycerol | 20 g |
| Purified water | q.s. to 100 ml |

Dissolve dextrorphan tartrate in an aliquot of water; dissolve parabens in glycerol and add this solution to the previous one. Bring to full volume.

Example 2

| | |
|---|---|
| Dextrorphan tartrate | 10 g |
| Hydroxypropylmethylcellulose | 0.5 g |
| Methyl p.hydroxybenzoate | 0.08 g |
| Propyl p.hydroxybenzoate | 0.02 g |
| Glycerol | 10 g |
| Purified water | q.s. to 100 ml |

Dissolve parabens in glycerol.

In 70% of water, dissolve at 40° C. dextrorphan tartrate and hydroxypropylmethylcellulose. At room temperature, add the two solutions to each other. Bring to full volume with water.

Example 3

| NASAL GEL | |
|---|---|
| Dextrorphan tartrate | 15 g |
| Carboxypolymethylene | 1 g |
| Propylene glycol | 20 g |
| Methyl p.hydroxybenzoate | 0.08 g |
| Propyl p.hydroxybenzoate | 0.02 g |
| Triethanolamine | 1.10 g |
| Purified water | q.s. to 100 ml |

In an aliquot of water, dissolved is dextrorphan tartrate and added is carboxypolymethylene.

Parabens are dissolved in propylene glycol; the solution obtained is added to the previous one.

By using the residual amount of water, dissolve triethanolamine; add this solution to the previous one, with careful mixing and stirring.

The gel is applied as a normal ointment for nasal use.

Example 4

| EMULSION | |
|---|---|
| Dextrorphan tartrate | 15 g |
| Cetylstearyl alcohol | 18 g |
| Esters of a polyol and fatty acids | 9 g |
| Distilled water | 55 g |

Dextrorphan tartrate is dissolved at 80° C. in 55 g of distilled water. Cetylstearyl alcohol and the esters of a polyol and fatty acids are melted at 80° C. with stirring in a suitable equipment.

To this mixture, the previously prepared solution is added with stirring at 80° C. stirring is continued at room temperature, until a homogeneous mixture is obtained.

Example 5

| SALVE | |
|---|---|
| Dextrorphan tartrate | 15 g |
| Carboxypolymethylene | 1 g |
| Triethanolamine | 1.25 g |
| Methyl p.hydroxybenzoate | 0.08 g |
| Propyl p.hydroxybenzoate | 0.02 g |
| Liquid paraffin | 10 g |
| Vaseline oil | 5 g |
| Castor oil | 5 g |
| Purified water | q.s. to 100 g |

Dextrorphan tartrate, and then, with stirring, carboxypolymethylene is dissolved in an aliquot of water. The solution is then added of triethanolamine in the residual amount of water: the blend is carefully mixed and is heated to 65° C.

Separately, a solution has been obtained by heating to 65° C. liquid paraffin, vaseline oil and castor oil.

The oily solution is added to the aqueous solution, and stirring is continued, while their temperature is slowly decreased to room value.

The ointment is applied as a normal ointment for nasal use.

Example 6

| Dextrorphan tartrate | 10 g |
|---|---|
| Polyglycol esters of fatty acids | 20 g |
| Distilled water | q.s. to 100 g |

Dextrorphan tartrate is dissolved at 70° C. in distilled water. The polyglycolic ester of fatty acids is melted at 65° C. with stirring in a suitable vessel. To this compound, added is, with stirring, and at 65° C., the previously prepared solution.

The whole mass is stirred at room temperature, until a homogeneous mixture is obtained.

Example 7

| Dextrorphan tartrate | 15 g |
|---|---|
| Liquid paraffin | 8 g |
| Lanolin O.P. | 3 g |
| White Vaseline | q.s. to 100 g |

Melt the excipients, add dextrorphan tartrate, homogenize and cool to room temperature.

Example 8

| PRESSURIZED AEROSOL | |
|---|---|
| Dextrorphan tartrate | 10 g |
| Soybean lecithin | 0.6 g |
| Ethanol | 5.5 g |
| Frigen 113 | 20 g |
| Frigen 11/12/114 | 70.9 g |

Dextrorphan tartrate, previously pulverized, is dispersed in about 10 ml of absolute ethanol; soybean lecithin and the propellants are added, and the whole is conditioned inside aerosol cans.

What is claimed is:

1. Pharmaceutically acceptable composition suitable to achieve a systemic therapeutic response to antitussis in warm-blooded animals, comprising:
   (I) a therapeutically efficacious amount of salified dextrorphan, and
   (II) a pharmaceutically acceptable non-toxic excipient for intranasal administration per dosage unit.
2. Pharmaceutical composition as in claim 1, in the form of a nasal suspension.
3. Pharmaceutical composition as in claim 1, in the form of a nasal salve.
4. Pharmaceutical composition as in claim 1, in the form of a nasal cream.
5. Pharmaceutical composition as in claim 1, in the form of a nasal solution.
6. Pharmaceutical composition as in claim 1, in the form of a nasal gel.
7. Pharmaceutical composition as in claim 1, in the form of a sustained-release gel.
8. Pharmaceutical composition as in claim 1, in the form of nasal drops.
9. Pharmaceutical composition as in claim 1, in the form of a nasal spray.
10. A method for inducing therapeutic levels of dextrorphan in warm-blooded animals which comprises: administering an effective amount of a composition as in claim 1 intranasally.

* * * * *

UNITED STATES PATENT AND TRADEMARK OFFICE
CERTIFICATE OF CORRECTION

PATENT NO. : 5,019,579

DATED : MAY 28, 1991

INVENTOR(S) : Piero Del Soldato and Silvano Casadio

It is certified that error appears in the above-identified patent and that said Letters Patent is hereby corrected as shown below:

On The Title Page

The spelling of the assignee should be as follows:

[73] Assignee: Prodotti Formenti S.r.l.

Signed and Sealed this

Twentieth Day of October, 1992

Attest:

DOUGLAS B. COMER

Attesting Officer

Acting Commissioner of Patents and Trademarks